United States Patent [19]
Bredeweg

[11] 3,985,505
[45] Oct. 12, 1976

[54] COMBUSTION SYSTEM
[75] Inventor: Roger L. Bredeweg, Stevensville, Mich.
[73] Assignee: Leco Corporation, St. Joseph, Mich.
[22] Filed: Nov. 21, 1974
[21] Appl. No.: 525,998

[52] U.S. Cl. .................... 23/230 PC; 23/253 PC; 431/9
[51] Int. Cl.² .................................. G01N 31/12
[58] Field of Search ...... 23/230 PC, 253 PC, 232 C, 23/253 R, 230 M, 232 E, 254 E, 255 E, 232 R, 254 R; 431/9, 76, 115, 116

[56] References Cited
UNITED STATES PATENTS

| | | | |
|---|---|---|---|
| 3,647,385 | 3/1972 | Stephens | 23/230 PC |
| 3,649,202 | 3/1972 | Bajek et al. | 23/253 PC |
| 3,716,334 | 2/1973 | Pont | 23/230 PC |
| 3,810,738 | 5/1974 | Fleischmann | 23/230 R |
| 3,854,877 | 12/1974 | Csaky et al. | 23/230 PC |

OTHER PUBLICATIONS
Graff et al., Anal. Chem. 24, 878 (1952).

Primary Examiner—Robert M. Reese
Attorney, Agent, or Firm—Price, Heneveld, Huizenga & Cooper

[57] ABSTRACT

A combustion system includes a combustion furnace for combusting a solid or liquid specimen and converting it to a gaseous mixture. The furnace is positioned in a circulatory loop in which oxygen is introduced to complete the combustion of the specimen into a gaseous mixture which is circulated through the furnace to fully oxidize the specimen and maintain the specimen gas concentration level constant during a measurement interval. To facilitate circulation of the gases in the loop, a circulation pump is employed in the flow path. In one embodiment, a detector is included in the loop while in alternative embodiments, an aliquot of the specimen gases is removed for analysis by a detector outside of the loop.

24 Claims, 4 Drawing Figures

COMBUSTION SYSTEM

BACKGROUND OF THE INVENTION

The present invention relates to a system including a combustion furnace for combusting a specimen into a gaseous sample for subsequent analysis.

In existing combustion-type analyzers such as Model No. CS-44, commercially available from Leco Corporation, the carbon and sulfur content of steel, for example, can be determined from a solid specimen which is positioned in an induction furnace and combusted to provide a gaseous sample. The gaseous sample is subsequently analyzed by an infrared detector to ascertain the carbon dioxide ($CO_2$) and sulfur dioxide ($SO_2$) concentrations which are then displayed as the carbon and sulfur content of the specimen. Certain aspects of such a system are disclosed in a pending U.S. patent application entitled COMBUSTION APPARATUS FOR ANALYTICAL INSTRUMENTS, Ser. No. 291,763, filed on Sept. 25, 1972, now U.S. Pat. No. 3,923,464, and assigned to the present assignee, the disclosure of which is incorporated herein by reference.

Such systems are open-ended in that a carrier gas is introduced into the combustion chamber of the induction furnace to oxidize the specimen and carry the specimen gas through an infrared cell and then exhaust it to the atmosphere. With such systems, therefore, the concentration of the specimen gas increases from near zero as combustion begins, to a peak period which diminishes rapidly as a function of time. The detecting and displaying devices thus are time dependent and must rapidly respond to the pulse of specimen gas to provide an accurate indication of the carbon and sulfur content of the specimen. To accomplish measurement, an integrator circuit is employed for integrating the electrical pulse developed by the infrared detector in response to the pulse of gas.

Such systems have proven effective although the detectors and circuits required to respond to the momentary pulse of specimen gas must, of necessity, have a relatively short time constant and, therefore, are subject to noise interference. Additionally, due to the open-ended flow of the gas through the system, in some cases incomplete combustion of the specimen into the constituent gases occurs. Also in such systems, the gas flow rate must be carefully regulated to maintain it constant such that electrical integration of the signal from the detector can be accurately undertaken and reproduced from sample to sample. In the CS-44 system, only $CO_2$ is measured to ascertain the carbon content of the sample, thus requiring the use of an expensive and troublesome catalytic converter for converting CO to $CO_2$.

SUMMARY OF THE INVENTION

The method and apparatus of the present invention overcomes the shortcomings of the existing systems by providing a system which includes a circulation loop for the carrier and specimen gases, which loop includes gas circulating means and a combustion furnace. Means are provided for introducing a carrier gas into the loop and for detecting the resultant specimen gas after combustion of the specimen has occurred. In one embodiment of the invention, an infrared detecting cell is included in the loop and also serves as a mixing chamber for the carrier and specimen gases from the combustion furnace. In another embodiment, means are provided for withdrawing an aliquot gas sample for analysis by an external detector. In one aspect of the invention, CO and $CO_2$ in the system are both detected and the results summed to provide a total carbon representative signal without the use of a costly and troublesome converter previously employed.

With the present system, the concentration of the specimen gas remains relatively constant over a longer period of time for measurement once combustion has been completed thereby permitting the use of electrical circuits which are less time dependent and, therefore, can be highly noise immune.

With this system, the flow rate of gases in the loop is not critical since the specimen gas concentration level remains relatively constant. Additionally, since the flow path is closed and gases are recirculated through the combustion chamber, complete combustion is assured and, therefore, full conversion of the specimen to its constituent gases. Such a system further provides for ease of calibration either by gas dosing in the closed loop which has a constant volume and is operated under constant pressure or by using a specimen of known concentration. Also, the carrier gas, such as oxygen, is conserved since the system is a closed loop.

These and other features and advantages of the present invention will become apparent upon reading the following description thereof together with the accompanying drawings in which:

DETAILED DESCRIPTION OF THE PREFERRED EMBODIMENT

Figure 1:
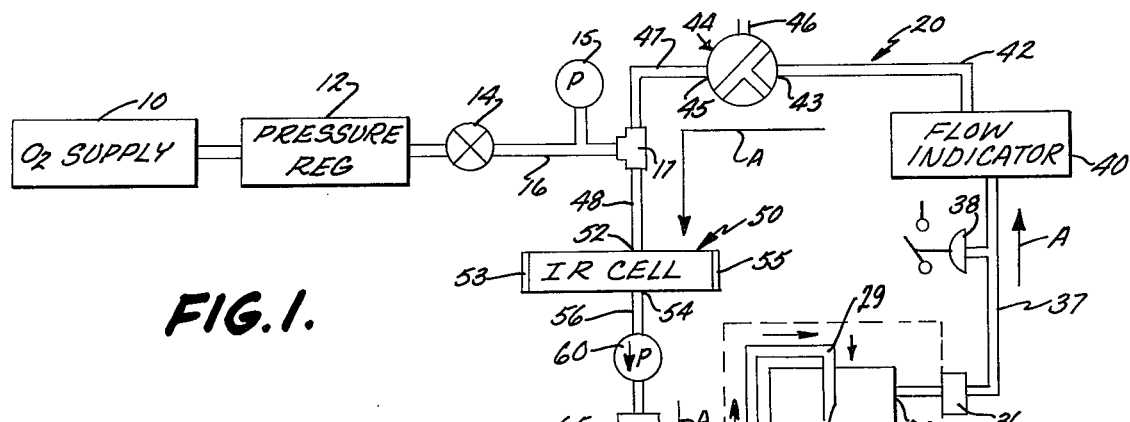
FIG. 1 is a block diagram of the components forming the gas flow loop of the system of one embodiment of the present invention.

Referring now to FIG. 1, the system includes a supply 10 of oxygen which is employed as the carrier gas as well as the oxidizing agent for the specimen. Gas from supply 10 is fed through a conventional pressure regulator 12 which regulates the pressure at approximately 4 psig. Oxygen from the regulator flows through an on-off valve 14 and into the system's closed loop 20 by a T-connector 17 which couples conduit 16 from valve 14 to conduits 47 and 48 in the loop. A pressure gauge 15 is coupled to conduit 16 and indicates the pressure of $O_2$ supplied to the system.

Loop 20 includes an induction-type furnace 25, shown schematically in the figure, which furnace is of substantially identical construction to a commercially available Leco Corporation induction furnace Model No. 760-200. The furnace includes an inlet 26 for carrier gas which is supplied to a combustion chamber 27 through a lower inlet 28 of the combustion chamber and a jet forming means 29 for directing a stream of oxygen downwardly into the mouth of a crucible 30 in which a specimen 32 is positioned. Gas flow from inlet 28 assures that all of the specimen gas is cleared from the combustion chamber 27 through an outlet port 34 as described in detail in the pending application identified supra. The combustion chamber includes sealable access means for providing access to the interior for inserting and removing crucibles and specimens while scaling the chamber, except for ports 28, 29 and 34, during combustion.

A dust trap 36 is coupled to outlet means 34 for filtering particulate material from the exit stream of the specimen gas. A conduit 37 couples the exit end of the dust trap 36 to a flow indicator 40 for monitoring the flow rate within the loop which can vary between 5 and 10 liters per minute. Indicator 40 is a ball-type device with a valve for adjusting the flow of fluid therethrough within the relatively wide usable range of this system. A pressure-actuated switch 38 is coupled to conduit 37. Switch 38 does not interfere with the flow of gases through conduit 37 but merely responds to the pressure in the conduit for providing a control function as described below. It is noted here that in the preferred embodiment, the conduits were ¼ inch Teflon tubing with standard fittings coupling the conduit sections to the various elements of the loop.

A conduit 42 couples the flow regulator to an electrically actuated three-way valve 44 including an inlet end 43, an exhaust 46 and an outlet 45. Valve 44 is positioned upstream of and in proximity to the carrier gas inlet junction 17. It is noted here that the flow of gases in loop 20 is in a direction indicated by the arrows identified by reference A in FIG. 1. Valve 44 is electrically actuated as described below, between a first position providing a flow path between inlet 43 and outlet 45 while closing off the exhaust 46 and a second position in which outlet 45 is blocked and exhaust 46 is opened. The second position is employed for purging the system prior to operation. Outlet 45 of valve 44 is coupled to fitting 17 by conduit 47 and then to an infrared cell 50 by conduit 48.

Cell 50 is a conventional axial-type infrared cell which comprises a 1000 cc cylindrical chamber which includes an inlet 52 and an outlet 54 for admitting and exhausting the specimen gas mixture therein. Cell 50 constitutes at least 50% of the total volume of the loop including the cell chamber. The cell chamber serves the dual function of acting as ballast for the loop. In the preferred embodiment, cell 50 was a 9 pass cell having an optical path of approximately 63 inches. The cell includes spherical mirrors of equal focal lengths facing one another at opposite ends of the chamber and spaced to provide 9 passes of radiation therebetween. Each mirror includes a calcium fluoride window at its center such that in the preferred embodiment, light enters the cell through one window and exits through the other, thus permitting the transmission of infrared radiation through the gas-filled cell.

The exit end 54 of cell 50 is coupled to a circulation pump 60 by means of conduit 56. Pump 60 is a diaphragm-type pump commercially available from Thomas Industries and is continuously operated to maintain the circulation of gases in loop 20. Coupled in series between the exit end of the pump 60 and the inlet 26 of the furnace is a septum 64 with a self-sealing membrane 65 for admission of a calibration gas sample into the loop or removal of an aliquot for analysis. Conduit 66 couples the exit end of septum 64 to the inlet 26 of furnace 25 to close the loop 20. It is noted here that during operation of the system shown in FIG. 1, the specimen gases do not enter the supply line 16 coupled to T-connector 17 inasmuch as the pressure of the loop is approximately equal to or very slightly below the pressure of the oxygen supplied through regulator 12. Accordingly, gases will not flow from the closed loop into conduit 16 during operation.

In the FIG. 1 embodiment, the infrared cell 50 is positioned in series with the loop 20. Associated with the infrared cell 50 is detection means for detecting the existence and concentration of gases within the cell. A detector arrangement which can be used with the infrared cell 50 within the loop 20 or with a substantially identical infrared cell 50' remote from the loop and into which an aliquot sample can be introduced, is now described in conjunction with FIG. 2.

Figure 2:
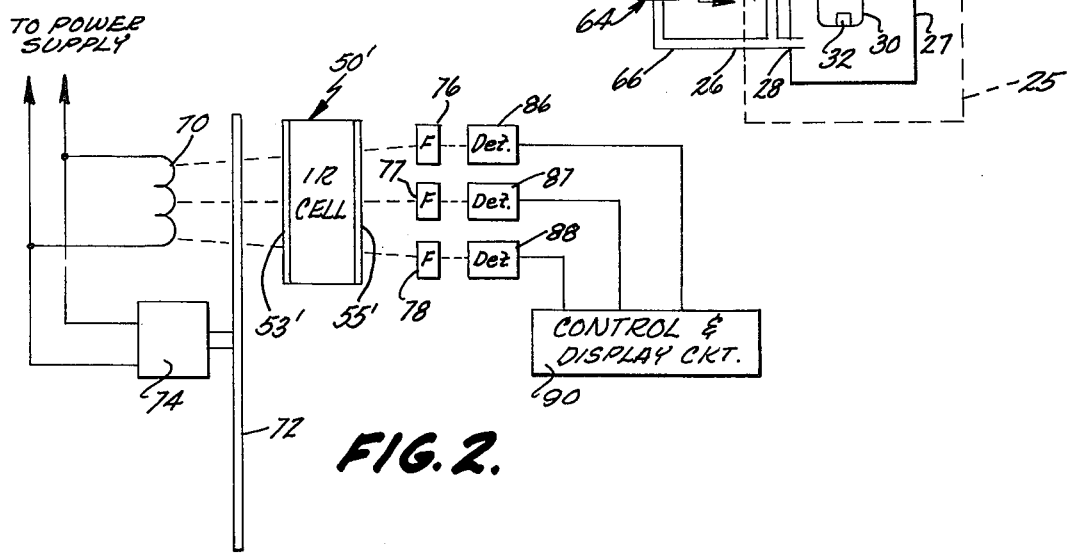
FIG. 2 is a block and schematic diagram of the detection means, control and display circuitry employed with the system shown in FIG. 1 or as a separate unit.

In FIG. 2, a broad band infrared light generator is provided and includes a coil 70 of nichrome wire coupled to a power supply for heating the coil to approximately 900°C for emitting infrared radiation. The radiation from coil 70 (shown as dashed lines) is chopped at 75 Hz by a rotating chopper disc 72 coupled to the output shaft of a motor 74, also coupled to the power supply. The pulses of 75 Hz infrared radiation are directed to the window 53' on the input side of the infrared cell, through the gas specimen within the cell, and exit at output window 55' of the cell. In the preferred embodiment, the analyzer is employed to detect the presence and percentage by weight of carbon and sulfur. Since carbon will, when combusted, form carbon monoxide (CO) and carbon dioxide ($CO_2$), and since the existent sulfur will form sulfur dioxide ($SO_2$), three transmission-type filters are employed to detect these three gases and develop signals which represent the weight of the carbon and sulfur forming the gases during the combustion process.

Thus, in the FIG. 2 embodiment, a 7.3 micron wavelength filter 76 is provided for $SO_2$, a 4.6 micron filter 77 is provided for CO, and a 2.7 micron filter 78 is provided for $CO_2$. Each of these filters is positioned near the output window 55' of the infrared cell such that the infrared radiation passing through the cell impinges upon the filters. Behind the filters are positioned associated broad band infrared detectors 86, 87 and 88 associated with filters 76, 77 and 78 respectively. Each of the filters is commercially available and transmits only frequencies associated with the gases mentioned above. The infrared cell, on the other hand, absorbs that portion of the infrared spectrum associated with the particular gas such that the signal detected will be a 75 Hz signal whose amplitude decreases with increased concentrations of the detected gas in the loop and, therefore, in the infrared cell. The detectors are pyroelectric detectors which are commercially available and are coupled to a control and readout circuit 90 described in detail in conjunction with FIG. 3. It is noted here that due to the greater conversion of carbon to $CO_2$ in the improved combustion apparatus of this invention, only approximately 2–3% of the carbon remains as CO. Thus, in analyzers not requiring accuracy available in the system of the preferred embodiment, the CO detectors and signal processing circuits can be omitted.

Figure 3:
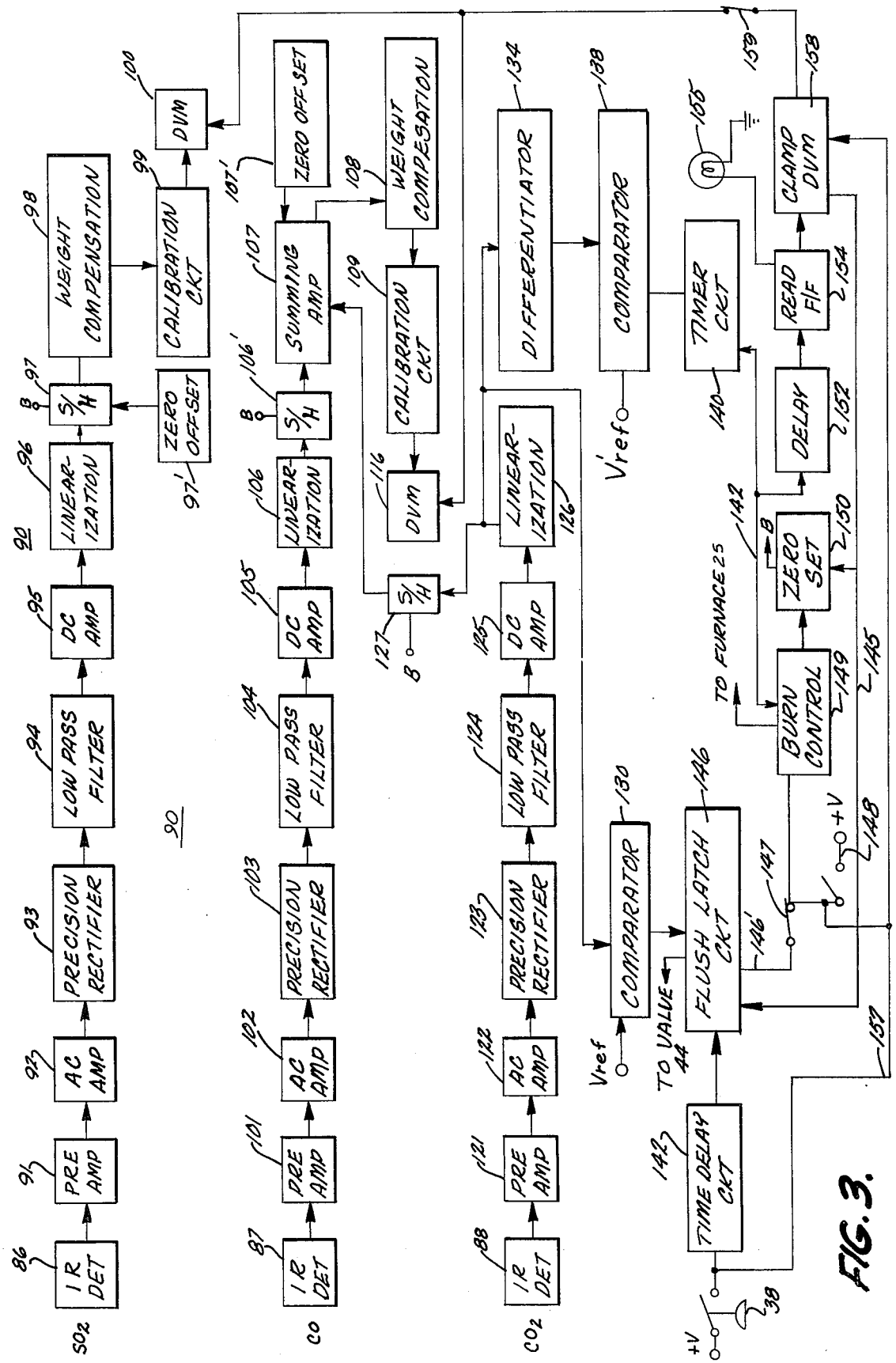
FIG. 3 is a detailed electrical circuit diagram in block form of the detectors, and control and display circuits shown in FIG. 2.

In order to develop a direct voltage level representative of the percentage carbon and percentage sulfur of the specimen, three discrete signal processing channels are employed and identified in FIG. 3 as an $SO_2$ channel, a CO channel and a $CO_2$ channel. Each of the channels has similar circuitry so a detailed description of only the $SO_2$ channel will be presented to fully describe the system.

The pyroelectric infrared detector 86 of the $SO_2$ channel is coupled to a preamplifier 91 whose output is coupled to an AC amplifier the 75 Hz amplitude modulated signals and applies them to a precision rectifier circuit 93. Circuit 93 is a full wave rectifier which is commercially available and rectifies the signal at the zero crossover point so that no signal loss occurs. The full wave rectified 150 Hz pulses resulting therefrom have a direct voltage level proportional to the concentration of the detected gas and are applied to a low pass filter 94. Filter 94 is conventionally designed to have a band pass of 0–10 Hz and thereby provide noise immunity for the system while filtering out the 150 Hz ripple and providing the desired direct voltage signal output. The resultant direct voltage output level from filter 94 is applied to a DC amplifier 95 which is a conventional operational amplifier and thence to a linearization circuit 96.

Circuit 96 is employed to compensate for the inherent nonlinearities in the absorption phenomena of the specimen gas to infrared radiation which follows Beers' Law to some extent. The Linearization circuit 96 comprises a logarithmic amplifier such as a commercially available type 755 device which is coupled to a zero offset circuit which provides a zero output with 100% transmission through cell 50 (which occurs with no specimen gas of the desired detected frequency). The logarithmic amplifier also applies its output to the input of a threshold amplifier having a series diode input such that the output remains constant until the bias point of the diode is reached. The zero offset output and the threshold amplifier outputs are applied to the input of a commercially available multiplier circuit type 732 whose output is the ouput of the linearization circuit 96. The $SO_2$ and $CO_2$ linearization circuits are very similar while the CO circuit is basically an operational amplifier with diode break similar to the linearization circuit employed in the Leco Corporation CS-44 analyzer.

The corrected direct voltage output level from linearization circuit 96 is applied to a sample and hold circuit 97 of conventional construction including a summing amplifier coupled to the input and output thereof and including a control input terminal B which receives signals, as described below, to hold the existent signal level at a zero level at an output terminal of the summing amplifier. A zero offset circuit 97' coupled to circuit 97 consists of an adjustable offset potential for compensating for a blank as described below under OPERATION. Circuit 97 provides a DC offset signal which is adjusted to zero level for no detected sulfur in a specimen being analyzed. The output of circuit 97 is coupled to a weight compensator circuit 98.

The weight compensator circuit 98 is substantially identical to the corresponding circuit employed in the previously identified commercially available CS-44 analyzer. Circuit 98 basically comprises a resistive divider network which can be manually or automatically programmed by setting the calibrated resistors to the weight of the specimen positioned in the crucible for analysis, thus compensating for different weight specimens.

The weight compensator circuit 98 is coupled to a calibration circuit 99 which comprises a variable resistor for calibrating the system with a gaseous or solid specimen with a known concentration of sulfur and carbon. The operation of the calibration circuit will be described in greater detail below under OPERATION. The output of circuit 99 is coupled to a commercially available digital volt meter (DVM) 100 which displays the direct voltage applied thereto as the percentage by weight of sulfur.

The CO and $CO_2$ channels are similar to the $SO_2$ channel with the exception of the linearization circuitry differences noted above and have an output from the sample and hold circuits 106' and 127 applied to the input of a DC summing amplifier 107. The zero offset circuit 107' is coupled to 107 to perform a function similar to circuit 97'. Amplifier 107 combines the amplitude of the two input signals and applies them to a weight compensator circuit 108 identical to circuit 98. The output of circuit 108 is applied to a calibration circuit 109 similar to circuit 99 and thence to a separate digital volt meter 116. Thus, one display 100 is provided for the percentage of sulfur in the specimen while display 116 provides a digital readout of the carbon content which is the combination of carbon in the form of detected CO and $CO_2$. As noted earlier, since the CO forms only 2–3% of the total carbon content of the specimen with the improved system, in some applications where extreme accuracy is not required, the CO channel can be omitted if desired.

In order to automatically or manually control the operation of the system including the combustion furnace and valve 44 shown in FIG. 1, the remaining control circuitry of FIG. 3 is employed. Specifically, the output from the linearization circuit 126 associated with the $CO_2$ channel is applied to one input of a comparator 130 having its remaining input coupled to a DC reference voltage $V_{ref}$. Comparator 130 provides an output signal when the detected $CO_2$ concentration has reached a predetermined low level indicating that the system has been fully purged and applies the control signal to a flush latch circuit 146 which initiates the actuation of valve 44 to close exhaust opening 46 and open the exit end 45, thus closing the loop to the atmosphere and permitting circulation of gases around loop 20 of FIG. 1.

The output of linearization circuit 126 also is applied to a differentiator circuit 134 which differentiates the signal to provide a rate of change signal to a second comparator 138 having its remaining input terminal coupled to a DC reference voltage $V'_{ref}$. The output of comparator 138 is applied to the input of a resettable timer circuit 140. Timer 140 is of conventional construction and responds to a signal from circuit 138 which provides a positive indication that combustion is taking place to control the burn control circuit 149 to continue combustion for an additional 15 seconds to assure that complete combustion has taken place.

The control system includes a time delay circuit 142 which has an input coupled to pressure switch 38 such that when the system pressure of approximately 2 psig is reached, indicating that the furnace is closed, delay circuit 142 times out and applies a control signal to the flush latch circuit 146. Circuit 146 is a flip-flop which provides a control signal at its output terminal 146' upon receipt of a control signal from circuit 142 and when enabled by a signal from circuit 130.

Switch 147 is a manual/automatic switch coupling terminal 146' of circuit 146 to the input terminal of flip-flop circuit 149 which serves as the burn control circuit. When closed, this switch provides automatic operation once the pressure switch 38 is closed. For manual operation, switch 147 is open and switch 148, which is a push button momentary close switch, is actuated by the operator to apply a control signal to the burn control flip-flop 149.

The one output of circuit 149 is also coupled to the input of a zero set flip-flop 150 having an output terminal B coupled to the sample and hold circuits 97, 106' and 127. The output from timer 140 which resets the burn control flip-flop to terminate furnace operation, is also coupled to a 4 second delay circuit 152 which has an output coupled to a read flip-flop 154. Circuit 154 responds to the signal from delay circuit 152 to actuate a read light 155 and simultaneously actuate a DVM clamping flip-flop 158 having an output coupled to DVMs 100 and 116 through calibration switch 159. Switch 159 is normally closed during operation and opened for calibration as described below under OPERATION. Light 155 provides an indication to the operator that the data is being displayed by the DVMs 100 and 116 which are clamped to hold the incoming data. Circuit 158 is reset initially by the pressure switch signal on conductor 157 or manually by switch 148 coupled to the reset terminal clamp 158. One of the output terminals of flip-flop 158 is coupled via conductor 145 to reset the flush latch flip-flop for opening valve 44.

Having described the circuitry for processing the detected signals and displaying such signals on the DVMs, and the control circuitry for the system, a description of the operation of the system is now presented.

OPERATION

Before analyzing a steel specimen by placing it in crucible 30 (FIG. 1) and combusting the specimen, it is first desirable to run a blank to ascertain the amount of carbon and/or sulfur in a crucible and in the accelerator. This is achieved by placing an accelerator in the crucible, inserting the crucible in the furnace, closing the system and running the furnace through a cycle in the calibration mode and zeroing the output reading to compensate for carbon and/or sulfur in the crucible and accelerator which may affect the accuracy of the results when a specimen is being anaylzed. DVMs 100 and 116 are zeroed by adjusting zero controls 97' and 107', respectively, until a zero reading on each DVM is achieved. The operation of this cycle is basically the same as will be described below with reference to a calibration cycle.

Once a blank has been run, the furnace is opened and valve 44 actuated to permit the system to be purged from vent 46 by the oxygen flowing through loop 20 from source 10. After purging, the system is ready for calibration which can be accomplished either by gas dosing the system or by burning a specimen with a known percentage of carbon and sulfur in a crucible. A brief description of each is provided for a full understanding of the calibration process.

With gas dosing calibration, once the system is purged, the furnace is closed as is valve 44 to shut off the vent from exit end 46 and to provide a closed flow path in the loop. With the oxygen circulating in the loop, a syringe with a known concentration of the specimen gases (i.e., $SO_2$ and/or CO and $CO_2$) is injected into the loop through membrane 65 of septum 64. Thus, for example, for the 1200 cc total volume of the loop (including the 1000 cc infrared cell) of the preferred embodiment, a 20.7 cc volume of $CO_2$ is injected into the loop at standard temperature and pressure to provide a 1% calibration reading for carbon. Similarly, other volumes of gases can be employed to provide the calibration readout.

With the known concentration of gases recirculating the loop, and switch 159 opened such that live data is displayed on DVMs 100 and 116, the calibration circuits 99 and/or 109 are adjusted to provide the percentage weight readout corresponding to the known calibration sample.

Alternatively, a solid specimen with a known concentration of carbon and/or sulfur can be placed in a furnace crucible and a burn cycle run in which, as with gas dosing, the calibration controls for each detected specimen are adjusted to provide the display output corresponding to the known concentration.

Once calibration by either method is accomplished, the furnace is opened as is valve 44 to purge the system of calibration gas and a specimen 32 of unknown carbon and/or sulfur concentration is positioned in the crucible together with, in some cases, accelerators or the like to facilitate combustion as is well known in the art.

Figure 4:
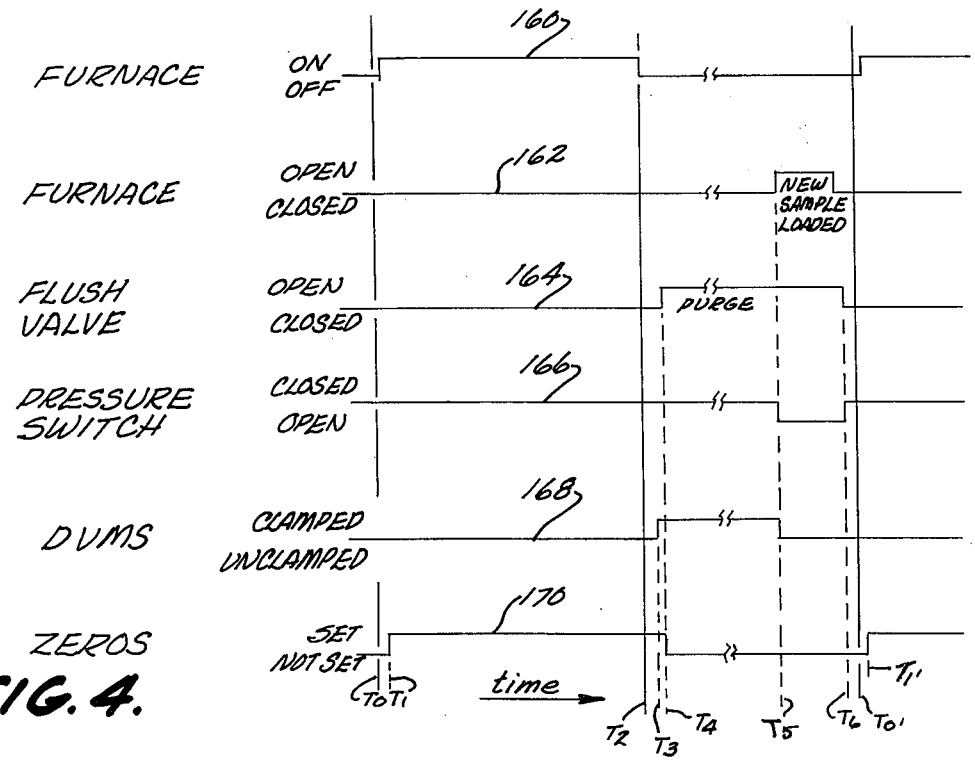
FIG. 4 is a timing diagram showing the operational state of various of the components of the system during a cycle of operation.

To facilitate a full understanding of the burn cycle of operation, the diagram of FIG. 4 is helpful. In FIG. 4, when waveform 160 is at the upper level, the furnace induction coil is actuated to combust the specimen within crucible 30. Waveform 162 represents the opening and closing of the combustion chamber which is opened to permit access to the crucible and closed to seal the combustion chamber within loop 20. Waveform 164 indicates the condition of the flushing valve 44 while waveform 166 indicates the actuation of pressure switch 38. Waveform 168 shows when the digital volt meters 100 and 116 are either unclamped where the data display is continuously being updated, or clamped once the final result is to be displayed continuously for a period of time. Finally, waveform 170 indicates the time at which the sample and hold circuit 97, 106' and 127 have their zeros set by circuit 150.

Along the time axis, shown in FIG. 4, $T_0$ represents the instant at which the automatic cycle is initiated once the furnace has been closed, $T_1$ the initiation of furnace operation, $T_2$ the end of furnace operation, $T_3$ the clamping of data in the digital volt meters, $T_4$ the opening of the valve for flushing the system once the data is displayed in the digital readouts, $T_5$ the opening of the furnace for reloading of a new sample, and $T_6$ the subsequent closing of the flushing valve after the purging cycle is completed. A new cycle is then initiated at $T_{0'}$. It is noted here that the signal channels are actuated continuously to supply data during the entire operational sequence of the furnace.

With a specimen 32 positioned in the crucible 30 at $T_0$, the furnace is closed to seal the combustion chamber in loop 20. Pressure switch 38 responds to pressures greater than 2 psig which occurs when the furnace is closed and initiates the operation sequence by providing a pulse to delay circuit 142 and clamp circuit 158 via conductor 157. The signal to circuit 158 unclamps the DVMs to permit the new specimen levels to be displayed. After a 4 second delay to permit continued purging through valve 44, circuit 142 provides an output pulse to the flush latch circuit 146. If a null is detected by comparator 130 indicating loop 20 is sufficiently clear of contaminates, latch 146 provides a signal to the electrically operated valve 44 to close off vent 46 and open the flow path in the closed loop. At the same time, circuit 146 will provide an output signal at output terminal 146'. With switch 147 in its normally closed (i.e., automatic operation) position, the output signal from circuit 146 is applied to the burn control latch circuit 149 which is a flip-flop which responds to apply a control signal to the furnace at $T_1$ and to timer 140. At about the same time, control 149 also applies a signal to flip-flop 150 which applies a control signal to circuits 97, 106' and 127 through interconnected terminals B. The sample and hold circuits respond to hold the detected residual signal level and subtract this level from the incoming signal to set at zero level any detected gas levels existent from sources other than the current specimen.

The commercially available furnace includes a control relay or other control device which responds to the signal from burn control circuit 149 to apply high frequency current to an induction coil for combusting the specimen in the crucible. Timer circuit 140 includes two separate timers of 30 and 15 seconds respectively. If after 30 seconds comparator 138 has not received a burn rate signal of a predetermined level indicating combustion has taken place, the second timer is started to continue the burn for a full 45 seconds. If, however, the comparator is actuated, the 30 second timer is stopped and the burn period is abbreviated to terminate at the end of 15 seconds. The output signal from timer 140 applied to circuit 149 via interconnection 142 terminates furnace operation in either event at point $T_2$ in FIG. 4.

By the end of furnace burn, the specimen gas has been homogenously mixed in loop 20 and the infrared detectors and associated signal processing circuits have actuated the DVMs 110 and 116 to red the concentration of sulfur and carbon, respectively, of the specimen.

At time $T_2$, the burn turn-off signal from timer circuit 140 is also applied to the input of delay circuit 152 which is a 4 second delay providing an output signal to the read flip-flop circuit 154 which actuates the read light 155 and the clamp DVM circuit 158 to clamp the signal level then displayed by DVMs 100 and 116. This occurs at time $T_3$. At this time, the specimen concentration is continuously displayed and the operator indicator light is illuminated to indicate to the operator that the data is ready to read.

The clamp DVM circuit 158 also applies, when actuated by a signal from circuit 154, a control signal to the zero set circuit 150 and the flush latch circuit 146 through conductor 145. At time $T_4$, the zero set control signal is removed from the sample and hold circuits 97, 106' and 127 and the flush latch circuit is actuated to open purge valve 44 to prepare the system for introduction of a subsequent sample. During this time, the DVMs are holding the previous data and continue to do so between the period $T_4$ to $T_5$ which can be any length of time as indicated by the broken segment in the FIG. 4 diagram.

At $T_5$, the furnace is opened and a new cycle of operation is initiated. The opening of the furnace opens pressure switch 38 to again unclamp the DVMs so that a new reading can be obtained from the new sample when loaded. At $T_6$, the furnace is closed initiating a new automatic cycle of operation.

It is noted that if manual operation is desired, switch 147 is opened and a push button 148 is employed to generate the desired cycle initiation pulse to the burn control and remaining circuits. The circuit operation, once initiated, is identical to that previously described.

It will become apparent to those skilled in the art that various modifications to the present invention can be made. Thus, for example, the furnace may be an induction-type furnace, as disclosed herein, a resistance heating furnace or other means for combusting a solid or liquid specimen to provide gaseous samples. Additionally, other type detectors can be employed. Such detectors may include, for example, thermocouple detectors, visible frequency or ultraviolet light detectors, emission detectors, atomic absorption detectors and the like. The arrangement of the various elements in the closed loop likewise may be varied depending upon the type of detector and furnace employed. These and other modifications to the preferred embodiment disclosed herein, however, will fall within the spirit and scope of the invention as defined by the appended claims.

The embodiments of the invention in which an exclusive property or privilege is claimed are defined as follows:

1. A method of promoting fast and complete combustion of an analytical specimen comprising the steps of:
   providing a combustion furnace for the combustion of a specimen; and
   circulating a gas through said combustion furnace in a loop during combustion of the specimen.

2. A method of combusting and analyzing a specimen by providing a gaseous sample comprising the steps of:
   inserting a nongaseous specimen into a combustion furnace;
   introducing an oxidizing gas into a closed flow path including said combustion furnace;
   actuating said combustion furnace for combusting said specimen;
   circulating gas in said closed flow path continuously during combustion and slightly thereafter;
   measuring the concentration of gas in said closed flow path after combustion; and
   blocking said closed flow path at one point and venting said closed flow path upstream the blocked are while continuing to introduce an oxidizing gas to purge said system of gas specimen prior to the insertion of a new specimen into said combustion furnace.

3. A combustion system for use in converting nongaseous specimens into gases for subsequent analysis comprising:
   a combustion furnace including a combustion chamber for receiving a specimen, said combustion chamber including gas input and gas output means;
   circulation means coupling said output and input means of said combustion chamber for circulating gases through said combustion chamber in a continuous loop during combustion of a specimen;
   means for introducing a gas into said loop for circulation of said gas around said loop during combustion; and
   said loop including means for venting said loop to the atmosphere for purging said loop.

4. The system as defined in claim 3 and further including detection means coupled to said circulating means in the flow path of gases in said loop for detecting the concentration of at least one predetermined gas.

5. The system as defined in claim 3 wherein said circulation means comprises a pump and conduit means coupling said pump to said input and output means of said combustion chamber.

6. The system as defined in claim 5 wherein said gas is an oxidizing gas and said means for introducing a gas comprises a source of oxidizing gas and means coupling said source to said conduit means for introducing said oxidizing gas into said loop at a substantailly constant positive pressure.

7. The system as defined in claim 6 and further including septum means coupled to said conduit means for introducing and withdrawing a gaseous sample into and from said loop respectively.

8. The system as defined in claim 7 and further including detection means coupled to said conduit means for detecting the concentration of at least one predetermined gas.

9. The system as defined in claim 8 wherein said detection means includes an infrared cell coupled to said conduit means in said loop, a source of infrared radiation for directing infrared radiation through said cell, filter means positioned in the path of said infrared radiation once said radiation has passed through said cell, said filter means selected to transmit radiation corresponding to said predetermined element, and radiation detector means positioned to receive radiation transmitted by said filter means and generate electrical signals in response thereto.

10. The system as defined in claim 9 and further including circuit means coupled to said radiation detector means and to said furnace for controlling said furnace and for displaying the percentage weight of a predetermined element associated with said predetermined gas.

11. A combustion system for combusting a solid or liquid specimen into a gaseous state for subsequent analysis, said combustion system comprising:
   a combustion furnace including a combustion chamber for receiving a specimen;
   a circulating pump for gases;
   means for coupling said circulating pump to said combustion furnace to define a substantially continuous gas flow path in a closed loop for circulating gaseous products of combustion through said combustion chamber and around said loop in a single direction for homogenizing the gases therein during combustion of a specimen in said furnace; and
   means for introducing a carrier gas into said loop.

12. A combustion system for oxidizing a solid or liquid specimen into a gaseous state for subsequent analysis, said combustion system comprising:
   a combustion furnace including a combustion chamber for receiving a specimen;
   a circulating pump for gases;
   means for coupling said circulating pump to said combustion furnace to define a closed loop for circulating gaseous products of combustion through said combustion chamber during combustion of a specimen;
   means for introducing an oxidizing gas into said loop; and
   valve means positioned in said loop in proximity with and upstream of said introducing means such that said valve means can be actuated to vent said loop and permit said oxidizing gas to purge said loop.

13. The system as defined in claim 12 wherein said valve means comprises a three-way valve movable between a first position in which gas passes through said valve and circulates in said loop and a second position in which said valve blocks said loop and vents said loop adjacent the block.

14. The system as defined in claim 13 and further including detection means including at least an element positioned in said loop for detecting the concentration of at least one predetermined gas.

15. The system as defined in claim 14 wherein said detection means comprises an infrared light source and detector, and wherein said element comprises a chamber coupled in said loop and having window means for permitting radiation from said source to pass through gases in said chamber and exit said chamber to impinge upon said detector.

16. A system for analyzing a solid or liquid specimen by converting it to a gaseous state comprising:
   an induction furnace for combusting a specimen;
   detection means coupled to said combusting means;
   circulation means coupled to said combusting and detection means for circulating gases in a closed loop through said detection and combusting means during combustion of a specimen in said induction furnace;
   a source of carrier gas;
   means coupling said source to said conduit means for introducing said carrier gas into said loop at a substantially constant positive pressure; and
   means for venting said loop to the atmosphere for purging said loop.

17. The system as defined in claim 16 wherein said circulation means includes gas a pump and conduit means coupling said pump, said induction furnace combusting means and said detection means in a closed loop.

18. A system for analyzing a solid or liquid specimen by converting it to a gaseous state comprising:
   means for combusting a specimen;
   detection means coupled to said combustion means;
   circulation means including a pump and conduit means coupling said pump, said combusting means and said detection means in a closed loop for circulating gases in a closed loop through said detection and combusting means during combustion of a specimen in said combusting means;
   a source of oxidizing gas and means coupling said source to said conduit means for introducing said oxidizing gas into said loop at a substantially constant positive pressure; and
   valve means positioned in said loop in proximity and upstream of said introducing means such that said valve means can be actuated to vent said loop and permit said oxidizing gas to purge said loop.

19. The system as defined in claim 18 wherein said valve means comprises a three-way valve movable between a first position in which gas passes through said valve and circulates in said loop and a second position in which said valve blocks said loop and vents said loop adjacent the block.

20. The system as defined in claim 19 wherein said detection means includes an infrared cell coupled to said conduit means in said loop, a source of infrared radiation for directing infrared radiation through said cell, filter means positioned in the path of said infrared radiatin once said radiation has passed through said cell, said filter means selected to transmit radiation corresponding to a predetermined element, and radiation detector means positioned to receive radiation transmitted by said filter means and generate electrical signals in response thereto.

21. The system as defined in claim 20 wherein said infrared cell comprises a chamber coupled to said conduit means and including window means for permitting radiation to pass through said cell, said chamber comprising at least 50% of the total volume of said loop.

22. The system as defined in claim 21 and further including circuit means coupled to said radiation detector means and to said furnace for controlling said furnace and for displaying the percentage weight of said predetermined element.

23. A system for determining the carbon content of a steel specimen comprising:
   a combustion furnace including a combustion chamber for receiving a steel specimen and for combusting said specimen to convert carbon therein to CO and $CO_2$ gases;
   circulating means coupled to said combustion furnace to define a loop and for circulating gases in said loop;
   means for selectively venting said loop to the atmosphere such that by-products of combustion can be purged from said loop;
   detection means including an element positioned in said loop and including a first detector for detecting the CO concentration in said loop and a second detector for detecting the $CO_2$ concentration in said loop; and
   circuit means coupled to said first and second detectors for summing the outputs thereof and for displaying the total percentage of carbon content of said specimen.

24. An analyzer for the simultaneous determination of carbon and sulfur in a specimen comprising:
   a combustion furnace including a combustion chamber for receiving a specimen and combusting said specimen, said combustion chamber including gas inlet and gas outlet means;
   a pump for pumping gases;
   detection means for detecting $So_2$, CO and $CO_2$ gases;
   conduit means coupling said combustion chamber, said pump and said detection means in a loop such that said pump continuously circulates gases through said loop;
   means for supplying oxygen to said loop under positive pressure;
   flush valve means coupled in said loop upstream the flow of gases from said oxygen supplying means and actuatable between a first position providing a gas flow path in said loop and a second position which blocks the gas flow in said loop and vents said loop; and
   circuit means coupled to said furnace and to said detection means for actuating said furnace and displaying the carbon and sulfur concentration of said specimens.

* * * * *

UNITED STATES PATENT AND TRADEMARK OFFICE
CERTIFICATE OF CORRECTION

PATENT NO. : 3,985,505

DATED : October 12, 1976

INVENTOR(S) : Roger L. Bredeweg

It is certified that error appears in the above-identified patent and that said Letters Patent are hereby corrected as shown below:

Column 3, line 6:
 "scaling" should be --- sealing ---.
Column 3, line 45:
 After "as" insert --- a ---.
Column 5, line 5:
 After "amplifier" insert --- 92 which amplifies ---.
Column 5, line 24:
 "Linearization" should be ---linearization---.
Column 7, line 23:
 After "terminal" insert --- of ---.
Column 8, Line 40:
 "circuit" should be --- circuits ---.
Column 9, line 34:
 "red" should be --- read ---.
Column 10, line 40:
 "are" should be --- area ---.
Column 11, line 5:
 "substantailly" should be ---substantially---.
Column 12, line 29:
 "gas a" should be --- a gas ---.
Column 12, line 32:
 "combusting means" should have been deleted per Amendment A.
Column 12, line 63:
 "radiatin" should be --- radiation ---.
Column 14, line 11:
 "So$_2$" should be --- SO$_2$ ---.

Signed and Sealed this

Twenty-second Day of February 1977

[SEAL]

Attest:

RUTH C. MASON
*Attesting Officer*

C. MARSHALL DANN
*Commissioner of Patents and Trademarks*